United States Patent [19]
Kessler

[11] Patent Number: 5,898,034
[45] Date of Patent: Apr. 27, 1999

[54] PSORIASIS MEDICATION AND APPLICATION FOR REMISSION AND/OR CURE OF PLAQUE PSORIASIS

[76] Inventor: Kenneth D. Kessler, 3020 St. Babette La., St. Charles, Mo. 63301

[21] Appl. No.: 09/083,627

[22] Filed: May 23, 1998

[51] Int. Cl.⁶ ...................................................... A61K 31/70
[52] U.S. Cl. ................................................................. 514/31
[58] Field of Search .................................................. 514/31

[56] References Cited

U.S. PATENT DOCUMENTS 5,762,945  6/1998  Ashley et al. ........................... 424/401

FOREIGN PATENT DOCUMENTS

2085462 AA  6/1994  Canada ..................................... 514/31

*Primary Examiner*—Jerome D. Goldberg

[57] ABSTRACT

A medication and application for the remission and/or cure of the disease of Psoriasis. Their are no other anti-fungal Psoriasis creams or medications of this type and style available on the market utilizing this form, format or application method.

1 Claim, No Drawings

PSORIASIS MEDICATION AND APPLICATION FOR REMISSION AND/OR CURE OF PLAQUE PSORIASIS

CROSS-REFERENCE TO RELATED APPLICATION

Not applicable

STATEMENT REGARDING FEDERALLY SPONSORED RESEARCH OR DEVELOPMENT

Not applicable

BACKGROUND OF THE INVENTION

Psoriasis takes several forms: scaly, red patches of skin. Plaque Psoriasis have patches, which appear on the trunk and limbs, especially on the elbows, knees and the scalp; Postural Psoriasis has small pustules spread over the body; and Guttate Psoriasis, usually in children, is characterized by tear drop-shaped lesions. This unpredictable disease, which affects men and women equally, strikes people of all ages and can erupt anywhere on the body. Psoriasis lesions form when new skin cells are produced at a rapid rate.

I spent many months in the McDonnell-Douglas (now Boeing-McDonnell) technical research library researching my Plaque Psoriasis problem. I have proven beyond a reasonable doubt that I had a fungal-yeast infection of a microbial nature, deep in my skin. This fungal-yeast infestation of my skin cells (May be referred to as Candida albicans) caused my skin cell reproductive cycle to be disrupted drastically.

Normal skin reproduction rate is approximately every 28 days for a complete reproductive cycle. With Psoriasis, a three too 5-day cell reproduction rate is normal.

BRIEF SUMMARY OF THE INVENTION

I developed an application in 1986 using a FDA approved anti-fungal medication (Nystatin, mixed with Vaseline) to address this fungal-yeast problem, and it worked. Eleven years later, now time tested, and still free from the symptoms of Plaque Psoriasis, I offered this find to McDonnell-Douglas aerospace but the company declined. I received from the McDonnell-Douglas company a release of invention after several months of research by the companies legal department (Enclosure #1 of 1).

DETAILED DESCRIPTION OF THE INVENTION

This is an FDA approved prescription medicine and is an anti-fungal drug. This medication is listed in the physicians desk reference. The Nystatin is prepared with equal amounts of Vaseline or a 1:1 ratio. Nystatin is commercially available through a doctors prescription in 60 Cc's (2 Oz) or 400 Cc's (1 pint) 100,000 units per mil/Cc. (Also available in an oral suspension). I used a 60 Cc's (2 Oz) of Nystatin, mixed with an equal amount of Vaseline.

The mixture was retained in another closed container and refrigerated. Keeping the Vaseline cool, maintain the gel-like consistency and in addition, it feels great being applied to the infected area.

My Plaque Psoriasis problem was on the hand's, knees and elbows. I purchased a pair of surgeons plastic gloves and applied the Nystatin cream mixture liberally on my hand's and put on the gloves. I did this at bedtime. This process was repeated nightly until the Psoriasis was cleared. For my knees and elbows the above process was repeated except I enclosed the medicated areas with a clear plastic wrap. I taped the edges of the plastic wrap (top and bottom) so the area stays covered during the night. Reason for all of this is:

By covering up the affected areas at night, the skin pores open. The body heat changes the Vaseline to an oil. The medication and Vaseline are taken deep into the skin. After removing the plastic gloves (or wrap) the following morning, the skin pores closed, retaining the oil and medication. In my case, I could see the Psoriasis disappear daily. It took 3 days and my Plaque Psoriasis was gone from my hands knees and elbows. This Nystatin usage and application is suitable with any oil base or suitable carrier.

Therefore, I wish to ask this utility (application) patent to cover and include all applicable oil-based materials (Synthetic or otherwise, none being specifically identified in this application) which could be used for and/or with this type and form of application, style and delivery of this medication (Nystatin) and the applied concept, technique and method described here within this application in its entirety. Any and all other delivery systems/applications for this medication (Nystatin) and its intended or implied purpose, pertaining, implied or specifically directed to a skin disorder or Psoriasis, in and above the current procedure as described in this document and application for patent.

My invention is:

1. A method for treating psoriasis on skin comprising administering to the infected skin an effective amount of nystatin and vaseline in a 1:1 ratio.3.

* * * * *